United States Patent [19]

Inoue et al.

[11] Patent Number: 4,772,470
[45] Date of Patent: Sep. 20, 1988

[54] ORAL BANDAGE AND ORAL PREPARATIONS

[75] Inventors: Yuichi Inoue; Tetuo Horiuchi; Kenji Hsaegawa; Koichi Nakashima; Takashi Tsuyoshi, all of Osaka, Japan

[73] Assignees: Nitto Electric Industrial Co., Ltd.; Sunstar Inc., both of Japan

[21] Appl. No.: 855,565

[22] Filed: Apr. 25, 1986

[30] Foreign Application Priority Data

Apr. 27, 1985 [JP] Japan .................................. 60-91580
Apr. 27, 1985 [JP] Japan .................................. 60-91581

[51] Int. Cl.$^4$ .............................................. A61K 31/78
[52] U.S. Cl. ........................................ 424/435; 424/81
[58] Field of Search .................. 424/434, 435, 448, 81

[56] References Cited

U.S. PATENT DOCUMENTS 4,249,531 2/1981 Heller et al. ......................... 424/435

FOREIGN PATENT DOCUMENTS

| 81987 | 6/1983 | European Pat. Off. . |
| 0106107 | 4/1984 | European Pat. Off. ............ 424/435 |
| 122344 | 10/1984 | European Pat. Off. . |
| 2133709 | 1/1973 | Fed. Rep. of Germany . |
| 2497098 | 7/1982 | France . |
| 59-196814 | 8/1984 | Japan .................................. 424/435 |
| 59-186913 | 10/1984 | Japan .................................. 424/435 |
| 186913 | 10/1984 | Japan . |
| 2086224 | of 1882 | United Kingdom . |

Primary Examiner—Joseph L. Schofer
Assistant Examiner—Peter F. Kulkosky
Attorney, Agent, or Firm—Sughrue, Mion, Zinn, Macpeak, and Seas

[57] ABSTRACT

An oral bandage comprising a soft adhesive film comprising a mixture of a polycarboxylic acid and/or a polycarboxylic acid anhydride and a vinyl acetate polymer in a compatible state, and an oral preparation comprising such an oral bandage having incorporated therein a topical drug are disclosed. The oral bandage or preparation exhibits strong adhesion of long duration when applied to the oral mucosa or teeth.

27 Claims, 1 Drawing Sheet

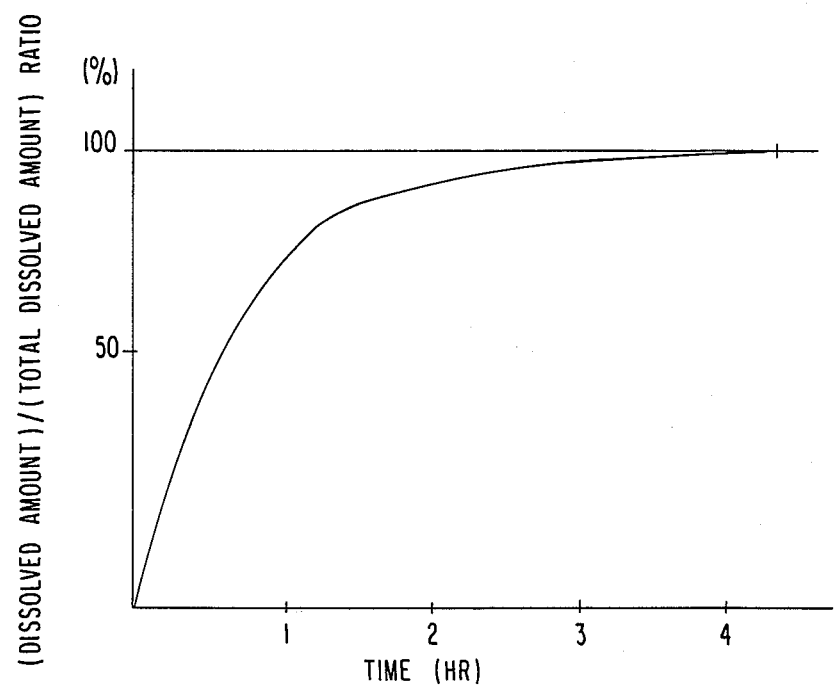

ORAL BANDAGE AND ORAL PREPARATIONS

FIELD OF THE INVENTION

This invention relates to an oral bandage that can be adhered to the oral mucosa to prevent a drug administered to the oral mucosa from running out and to cover or protect the affected part of the oral mucosa, and to oral preparations comprising such a bandage having incorporated therein a topical drug.

BACKGROUND OF THE INVENTION

In the field of dental and oral surgery, various topical preparations in the form of ointments or solutions have hitherto been administered to the oral mucosa for prophylaxis and therapy of oral diseases, such as periodontal disease, stomatitis, etc. The most serious problem in administering drugs to the oral mucosa is that the drug runs away in a short time by salivary secretion or through eating or drinking, thereby failing to fully exert its medical effects.

On the other hand, protection of the affected part in the oral cavity has scarcely been conducted because no effective oral bandage has been developed. As mentioned above, the continuous salivary secretion and taking foods and drinks constitute an insuperable barrier to realization of protection of the oral mucosa.

In recent years, many proposals have been made in an attempt to effectively administer a drug to the mucosa of the oral cavity, overcoming the above-described problems. Among them, proposals relevant to the present invention relate to preparations adhesive to the oral mucosa, which contain water-soluble high-molecular substances as an adhesive. When water-soluble high-molecular substances absorb a small amount of water, they become a viscous aqueous solution or gel having adhesion, though varying in extent with their kind. Making use of this property, various preparations adhesive to the oral mucosa have been proposed, including pastes as disclosed in Japanese Patent Publication No. 27491/81, sponges as disclosed in Japanese Patent Publication No. 25211/81, tablets as disclosed in Japanese Patent Publication No. 7605/83, sheets as disclosed in Japanese Patent Publication No. 16676/69 and Japanese Patent Application (OPI) No. 186913/84 (the term "OPI" as herein used means "unexamined published application"), and the like.

However, these conventional preparations only aim to adhesion to the oral mucosa to apply the drug contained therein. Therefore, adhesion enough to administer the drug to the mucosa for such a time period to allow the administration would be sufficient. In other words, these preparations do not possess strong adhesion for an extended period of time as required for an oral bandage. To the contrary, an oral bandage is intended to prevent running-off of the administered drug or to provide protections by adhesion to the affected or injured part of the oral cavity. Therefore, it is required to have strong and long-lasting adhesion to the oral mucosa which may be less adherable due to the administered drug or stomatorrhagia. Since both adhesive strength and duration of adhesion of the aforesaid conventional preparations adhesive to the oral mucosa are not so high as demanded for an oral bandage, application of bases used in these preparations to an oral bandage can never satisfy the above-described requirements of an oral bandage. The conventional adhesive tapes which are intended to be applied to the skin cannot be, of course, used as an oral bandage because they have no adhesion to a wet surface like the oral mucosa.

An oral bandage is required to have not only strong and long-lasting adhesion to the oral mucosa as described above but also softness sufficient to be adhered to an optional site of complicated shape in the oral mucosa and, in addition, safety from worsening of the injury due to irritation. However, an oral bandage having such performance characteristics has not yet been developed.

SUMMARY OF THE INVENTION

The present invention has been completed in the light of the above-described situations.

Accordingly, an object of this invention is to provide an oral bandage having high adhesive strength for a prolonged period of time and softness with which to adhere to an optional site of the oral mucosa or teeth.

Another object of this invention is to provide an oral preparation adhesive to the oral mucosa by which an active ingredient can be surely and effectively administered to the oral mucosa.

The above objects can be accomplished by an oral bandage comprising an adhesive film or a composite of such an adhesive film and a soft film support, said adhesive film comprising a mixture of a polycarboxylic acid and/or a polycarboxylic acid anhydride and a vinyl acetate polymer in a compatible state and an oral preparation comprising such an oral bandage having incorporated therein a topical drug.

The term "compatible state" as herein used means such a state that the polycarboxylic acid and/or polycarboxylic acid anhydride (hereinafter simply referred to as "polycarboxylic acids") and the vinyl acetate polymer (hereinafter referred to as polyvinyl acetate) are uniformly dissolved in each other without forming small individual regions due to phase separation.

Water-soluble high-molecular compounds, such as polycarboxylic acids and polycarboxylic acid anhydrides have per se a shape retention property. When they absorb a small amount of water, they exhibit strong adhesiveness but soon take up excess water to cause reduction in viscosity and degradation, thus resulting in losing their adhesiveness as being substantially dissolved in water. Moreover, since polycarboxylic acids in a dissolved state are acidic, they heavily irritate the sensitive injured part of the oral mucosa to cause worsening of the condition.

The present inventors have conducted extensive investigations on water-insolubilization of the above-described water-soluble high-molecular compounds, such as polycarboxylic acids, polycarboxylic acid anhydrides, etc., aiming at effective utilization of these compounds exhibiting excellent adhesion upon absorption of water as an oral bandage, while eliminating the above-described disadvantages, i.e., loss of adhesion due to over-absorption of water and irritation on the injured part. As a result, it has now been found that polycarboxylic acids and polyvinyl acetate are compatible with each other, and mixing of these two components in a compatible state substantially realizes water-insolubilization of the polycarboxylic acids without impairing the strong adhesion upon water absorption. Therefore, even if such a compatible mixture of the two components is shaped into a thin and soft film, it can exert strong adhesion for an extended period of time without undergoing degradation due to water absorption in a wet state.

It has further been found that incorporation of a basic substance (salts or bases) capable of neutralizing the polycarboxylic acids into the above-described compatible mixture can further relieve the irritation on the injured part of the oral mucosa.

It has furthermore been found that incorporation of topical drugs into adhesive film and/or film support comprising the above-described compatible mixture can provide film-like oral preparations retaining the strong adhesion, by which the drug can be surely, simply and effectively administered to the oral mucosa, thus establishing prevention and treatment of oral diseases.

BRIEF DESCRIPTION OF THE ACCOMPANYING DRAWING

The accompanying drawing is a characteristic curve of (dissolved amount)/(total dissolved amount).

DETAILED DESCRIPTION OF THE INVENTION

The soft films comprising a compatible mixture of the polycarboxylic acids and polyvinyl acetate according to the present invention does not show adhesion in a dry state but comes to exhibit strong adhesion upon water absorption, such adhesion being substantially unchangeable even when immersed in water. Such a characteristic can first be manifested when the polycarboxylic acids and polvinyl acetate are in a compatible state, not appearing when they are not in a compatible state.

As described above, the mixture of the polycarboxylic acids and polyvinyl acetate in a compatible state exhibit characteristics unpredictable from those of a mixture in a phase-separated state. More specifically, a film in a phase-separated state is turbid, whereas a film in a compatible state has such a high transparency that no independent small region is observed under an optical microscope. Further, when immersed in water, the polycarboxylic acids is dissolved out from the film in a phase-separated state, resulting in degradation as a whole; while the film in a compatible state only undergoes uniform swelling with very little elution of the polycarboxylic acids into water, which indicates that the polycarboxylic acids is substantially water-insolubilized. The compatible state (compatibility) of the polycarboxylic acids and polyvinyl acetate can be determined by making use of insolubilization of polycarboxylic acids.

When a basic substance capable of neutralizing polycarboxylic acids is mixed with the abovedescribed compatible mixture, the state of its mixing has no substantial influence on the adhesion property. Therefore, the basic substance may be mixed either in a compatible state or in a coarse dispersion.

Compatibility between the polycarboxylic acids and polyvinyl acetate can be clearly observed if the mixture consists of only these two components as mentioned above. However, differences in compatibility become unclear in those mixtures containing a basic substance having a neutralizing effect. In other words, in a mixture containing a basic substance, the mixing state of the basic substance being not restricted, even if the polycarboxylic acids and polyvinyl acetate are in a compatible state, the basic substance, if being mixed in a coarse dispersion, makes the film turbid. Thus, the mixing state of the polycarboxylic acids and polyvinyl acetate cannot always be observed visually or under an optical microscope.

Nevertheless, as described above, it has been confirmed that water-solubility of polycarboxylic acids can be markedly inhibited in a compatible mixture with polyvinyl acetate and that such a compatible mixture is uniformly swollen without degradation even when immersed in water for a considerably long period of time. This properly can be recognized irrespective of whether a basic substance having a neutralizing effect be present or not.

Accordingly, this property can be made use of in determination of compatibility between polycarboxylic acids and polyvinyl acetate. This method of determination can be regarded reasonable from the fact that the oral bandage according to the present invention can be adhered to the oral mucosa for a long period of time owing to the limited water-solubility of the polycarboxylic acids.

In the present invention, the compatibility between polycarboxylic acids and polyvinyl acetate is determined from the amount of dissolved polycarboxylic acids. That is, the compatible state as herein referred to specifically means that the dissolution ratio of polycarboxylic acids as obtained by the following method is 40% by weight or less. In the case of an oral bandage containing a salt having a neutralizing effect, it means that the dissolution ratio of polycarboxylic acids as obtained by the following method is 50% by weight or less, taking into account dissolving of the salt.

METHOD OF DETERMINING DISSOLUTION RATIO

A film comprising polycarboxylic acids and polyvinyl acetate is ground and weighed. The ground sample is put in a mesh bag and left to stand still in 300 times or more the weight of pure water at 20° C. for one hour. The bag is then taken out, and the amount of polycarboxylic acids dissolved out into the water is determined by neutralization titration or the like technique. This value is divided by the amount of the polycarboxylic acids initially contained in the film to obtain the dissolution ratio.

In the case when the film contains a basic substance, the dissolution ratio is obtained in the same manner as above except that the bag after the immersion is weighed to obtain the total amount of dissolved polycarboxylic acids and dissolved salt from, for example, weight reduction and this value is divided by the sum of the polycarboxylic acids and the basic substance initially contained in the film to obtain the dissolution ratio.

Since the oral bandage in accordance with the present invention comprises a soft film which is not adhesive in a dry state but shows adhesion only upon absorption of water, it can be stored as such without requiring any special storage conditions. On use, the oral bandage is sticked onto the oral mucosa whereupon it absorbs saliva or moisture of the mucous membrane to rapidly exert strong adhesion to the mucous membrane. Thus, it firmly adheres to the affected part or injured part of the oral cavity that is less adherable due to the drug administered, stomatorrhagia, and the like. This adhesion lasts for a markedly prolonged period of time, which is a well-marked characteristic of the present invention. Such adhesion of long duration can first be attained by the adhesive film comprising the polycarboxylic acids and polyvinyl acetate in a compatible state as set forth above.

The mechanism accounting for the long-lasting adhesion is not clear, but it is believed that the polycarboxylic acids contributes to adhesiveness to the wet mucosa and the polyvinyl acetate contributes to water resistance in a compatible mixture thereof, thus functioning in harmony to show adhesion of long duration.

The mixing state of the basic substance capable of neutralizing polycarboxylic acids has no influence on the adhesion, but the kind of the basic substance to be used exerts delicate influences on the adhesion and the like. For example, polyvalent metal salts, e.g., zinc oxide, calcium oxide, etc., function to reduce adhesion and to enhance water resistance, while monovalent metal salts, e.g., sodium acetate, etc., or a monovalent base, e.g., sodium hydroxide, triethanolamine, etc., functions to reduce water resistance and to enhance adhesion.

As described above, since the oral bandage in accordance with the present invention has adhesion of long duration, it can prevent the drug administered to the affected part of the oral cavity from running off to accelerate healing with a remarkably increased absorption of the drug and also give protection to the injured part of the oral cavity for a long period of time to expedite recovery.

Further, since the irritation due to eluted polycarboxylic acids can be reduced by adding a basic substance having a neutralizing effect to the adhesive film, such a situation that the injured part of the oral cavity becomes worse due to application of the oral bandage can be avoided.

In addition, the adhesive film according to the present invention is not merely composed of a water-soluble high-molecular substance but comprises a substantially water-insoluble soft film, in which polycarboxylic acids and polyvinyl acetate exist in a compatible state. Therefore, adhesion of long duration can be produced in a very thin film. In other words, too a thin film solely made of a water-soluble high-molecular substance is readily dissolved out in saliva in a short time to rapidly lose its adhesiveness so that a film made of such a material should have a considerably large thickness. However, a thick film produces a feeling foreign to the applied part and also reduces softness of the oral bandage. On the contrary, the oral bandage of the present invention does not require such a large thickness. thus giving no uncomfortable feeling.

The oral bandage according to the present invention can be produced by, for example, dissolving polycarboxylic acids and polyvinyl acetate in a solvent common to both and rapidly flow-casting the solution in a thin film, followed by drying.

The oral bandage containing a basic substance having a neutralizing effect according to the present invention can be produced by, for example, dissolving polycarboxylic acids and polyvinyl acetate in a solvent common to both, adding a basic substance capable of neutralizing the polycarboxylic acids to the solution, and rapidly flow-casting the mixture in a thin film, followed by drying. Incorporation of the basic substance may be carried out by dissolving in the solution or by dispersing a powderous basic substance in the solution. The above-described flow casting method is advantageous to easily produce a very thin film.

In the present invention, a topical drug can be incorporated into the oral bandage of the invention to obtain oral preparations. The method of incorporation is not particularly restricted, and usually comprises adding the topical drug directly or in the form of a solution to the solution of polycarboxylic acids and polyvinyl acetate, rapidly casting the composition in a thin film and drying.

Typical examples of the polycarboxylic acids which can be used in the present invention include acrylic acid polymers, methacrylic acid polymers and maleic anhydride polymers, either alone or in combinations threof. Specific examples of the acrylic polymers include an acrylic acid homopolymer and copolymers of acrylic acid and acrylic esters, e.g., butyl acrylate, 2-ethylhexyl acrylate, etc., methacrylic esters, e.g., methyl methacrylate, etc., or vinyl monomers, e.g., vinyl acetate, etc.; and copolymers, e.g., carboxyvinyl polymer. Examples of the methacrylic polymers include a methacrylic acid homopolymer and copolymers of methacrylic acid and comonomers as enumerated for the acrylic polymers Specific examples of the maleic anhydride polymers include copolymers of maleic anhydride and methyl vinyl ether, etc.

These compounds can be used either individually or in combination of two or more thereof. It is preferable that these polycarboxylic acids contain 20% by weight or more of a —COOH group in case of polycarboxylic acids or 16% by weight or more of a —CO—O—CO— group in case of polycarboxylic anhydrides.

The vinyl acetate polymer which can be used in the present invention typically includes a vinyl acetate homopolymer. In addition, copolymers of vinyl acetate and vinyl monomers, e.g., acrylic esters, and partial saponification products of a vinyl acetate homopolymer may also be employed. These vinyl acetate polymers may be used either individually or in combinations of two or more thereof. The polyvinyl acetate preferably has an average molecular weight (viscosity-average molecular weight) of not less than 60,000. Use of polyvinyl acetate having an average molecular weight less than 60,000 reduces water resistance of the adhesive, resulting in failing of the expected effects.

The basic substance which can be used for neutralizing polycarboxylic acids includes not only salts but bases. Typical examples of the salt include salts of metals and weak acids, metal oxides, metal hydroxides, amines, and mixtures thereof. Specific examples of the salt of metals and weak acids are salts of sodium, potassium, calcium, magnesium, etc. and carboxylic acids, e.g., acetic acid, lactic acid, citric acid, etc. Specific examples of the metal oxides are zinc oxide, calcium oxide, magnesium oxide, etc. Specific examples of the metal hydroxides are sodium hydroxide, potassium hydroxide, calcium hydroxide, magnesium hydroxide, etc. Specific examples of the amines are triethanolamine, diisopropanolamine, etc. These compounds can be used either alone or in combination. A preferred amount of the basic substance to be added widely varies depending on the kind thereof. In the case of using a polyvalent metal salt, for example, it is preferably added in an amount of from 0.2 to 0.8 equivalent based on the polycarboxylic acids. If its amount is less than 0.2 equivalent, the effect to relieve irritation on the injured part of the oral mucosa becomes insufficient. If it exceeds 0.8 equivalent, sufficient duration of adhesion can hardly be attained. In case of using a monovalent metal salt or a monovalent base, it is preferably added in an amount of from 0.03 to 0.2 equivalent based on the polycarboxylic acids. Amounts less than 0.03 equivalent reduce the effect to relieve irritation on the injured part, and amounts exceeding 0.2 equivalent reduce water resistance of the adhesive film, resulting in difficulty in obtaining sufficient adhesion.

The solvent common to the polycarboxylic acids and polyvinyl acetate includes lower alcohols, such as methanol, ethanol, etc.; mixed solvents comprising a lower alcohol in a larger proportion and a compatible organic solvent, such as acetone, ethyl acetate, etc.; and mixed solvents comprising a lower alcohol or the above-described mixed solvent and water. The mixed solvent of a lower alcohol and an organic solvent preferably contains not more than 30% by weight of the organic solvent because the organic solvent of more than 30% by weight makes it difficult to dissolve polycarboxylic acids. The mixed solvnet of a lower alcohol or a lower alcohol-organic solvent mixed solvent and water preferably contains not more than 30% by weight of water because a water content exceeding 30% by weight is liable to make it difficult to dissolve the polyvinyl acetate.

In the preparation of the oral bandage or oral preparations of the invention, it is preferable that the polycarboxylic acids to polyvinyl acetate mixing ratio fall within such a range that the value A as obtained according to the following formula ranges from 15 to 45:

$$A = \frac{\left(\begin{array}{c}\text{Weight of —COOH} \\ \text{in Adhesive Film}\end{array}\right) + \frac{5}{4}\left(\begin{array}{c}\text{Weight of —CO—O—CO—} \\ \text{in Adhesive Film}\end{array}\right)}{\left(\begin{array}{c}\text{Weight of Polycarboxylic Acids in Adhesive Film +} \\ \text{Weight of Polyvinyl Acetate in Adhesive Film}\end{array}\right)} \times 100$$

As the value A becomes larger, the adhesion to the mucous membrane increases, but the duration of adhesion tends to decrease. To the contrary, the smaller the value A, the lesser the adhesion, but the duration of adhesion tends to increase. If the value A is less than 15, sufficient adhesion is hard to obtain. If it exceeds 45, it becomes difficult to obtain sufficient duration of adhesion. Accordingly, the mixing ratio of polycarboxylic acids and polyvinyl acetate is preferably adjusted so that the value A falls within a range of from 15 to 45. Taking the case of using polyacrylic acid as a polycarboxylic acids for instance, with the proportion of polyacrylic acid in the adhesive film being between 24 and 72% by weight, the value A falls within the above-recited range to obtain good results.

When the polycarboxylic acids and polyvinyl acetate are dissolved in a common solvent, care should be taken so as to sufficiently dissolve the both components. On this occasion, concentrations of the polycarboxylic acids, polyvinyl acetate, etc. are not particularly limited. However, too a high concentration of the high-molecular substance makes the resulting solution highly viscous, and such a viscous solution is difficult to flow-cast in a film. Therefore, it is preferable to give care that the concentrations of the high-molecular substances may not exceed 40% by weight.

In the preparation of the adhesive film according to the present invention, the solution comprising the polycarboxylic acids and polyvinyl acetate and, if necessary, a basic substance and/or a topical drug is casted on an appropriate film, such as polyethylene-laminated paper, having been subjected to releasability-imparting treatment, and the casted film is rapidly dried with hot air in a drying oven or a drying tower. Suitable time and temperature in drying vary depending on the composition of a common solvent used, solid content of the solution, thickness of the cast film, the pressure and the like but, in general, preferably range from 60° to 120° C. in temperature and from 1 to 20 minutes in time under an atmospheric pressure. A very thin film that can be, as such, turned to use as an oral bandage can be thereby produced. The thickness of the resulting film is preferably be adjusted to a range of from 5 to 100 μm by controlling the amount of the casting solution, and the like. If a film thickness is less than 5 μm, it is difficult to obtain sufficient adhesion. A film having a thickness exceeding 100 μm tends to produce a feeling foreign to the mouth and to impair softness of the film.

As described above, the adhesive film in accordance with the present invention comprises a polycarboxylic acids and a vinyl acetate polymer not in a merely mixed state but in a compatible state with each other, in which the polycarboxylic acids is substantially water-insolubilized. Hence, even being very thin, it exerts strong adhesion for an extended period of time without suffering degradation due to water absorption. Besides, the film can easily be deformed according to the form of the oral mucosa and adhered thereto simply by pressing because of its softness.

The oral bandage and oral preparations according to the present invention may solely comprise the adhesive film but may further comprise a soft film support in combination.

The composite comprising the adhesive film and a support can be produced by laminating the adhesive film on a soft film support in a usual manner, such as hot pressing or by the use of an adhesive. Alternatively, the lamination can be carried out simultaneously with the preparation of the adhesive film by casting the film-forming composition on a soft film support, followed by drying. The latter process has an advantage over the former in simplifying the production procedure since hot pressing or adhesion with an adhesive is unnecessary.

The soft film support which can preferably be used in the present invention is substantially impermeable to water. Such a support typically includes plastic films, such as polyethylene, polyvinyl acetate resin, an ethylene-vinyl acetate copolymer, polyvinyl chloride, polyurethane, etc., metal foils, such as aluminum foil, tin foil, etc., laminates of cloth or paper and a plastic film, and the like. Of these, plastic films are preferred in view of safety and feeling on use. A preferred thickness of the film support is from 10 to 100 μm in view of handling properties and freedom from a foreign feeling on use. A thickness of the composite film, i.e., a total thickness of the adhesive film and the film support, is preferably in the range of from 30 to 150 μm. If it is less than 30 μm, handling properties and operation properties are deteriorated. A thickness exceeding 150 μm is liable to give a foreign feeling on use.

When the oral bandage of the invention contains a topical drug to obtain an oral preparation as described before, the topical drug may be incorporated into the adhesive film and/or the above-described film support. In the latter case, incorporation of the drug can be carried out by kneading with a resin material for the support, mixing the drug in the form of its solution with a resin material, absorbing onto a support, impregnating into a support, or a like method.

The topical drug which can be used in the present invention may be either solid or liquid at room temperature as long as it may be incorporated into the adhesive film or the film support by dissolving or dispersing.

Specific examples of the topical drugs to be used in the present invention are adrenal corticosteroids, e.g., Triamcinolone acetonide, Dexamethasone, Betamethasone, Prednisolone, Fluocinolone, Hydrocortisone, Beclomethasone, etc. and salts thereof; anti-inflammatory agents, e.g., Flurbiprofen, Ibuprofen, Diclofenac, Indomethacin, Bendazac, Flufenamic acid, Bufezamac, Cyclospoline, Clidanac, Glycyrrhizin, Ketoprofen, Piroxicam, Pranoprofen, Benzydamine, Ibuprofenpiconol, Etofenamate, Lysozyme, Chymotrypsin, Epidihydrocholesterine, Hinokitiol, α-Amylase, Azulene, Chlorophllin, Cromoglic acid, Tranilast, Serratiopeptidase, Pronase, Glucanase, Lithospermi Radix extract, etc. and salts thereof; antimicrobial agents, e.g., Acrynol, Cetyl pyridinium, Chlorhexidine, Domifen, Iodine, Monensin, Sanginalline, Metronidazol, Dequalinium, Tetracycline, Minocycline, Ofloxacin, Penicilline, Doxycycline, Oxycycline, Cefatrizin, Nystatin, Clindamycin, Fradiomycin sulfate, etc. and salts thereof; analgesics, e.g., Ethyl aminobenziate, Camphor, Eugenol, Dibucaine, Phenol, Menthol, Creosote, Diphenhydramine, Lidocaine, Tetracaine, Procaine, Cocaine, Piprocaine, Mepivacaine, Promoxin, Dicronin, Guaiacol, etc. and salts thereof; hemostatics, e.g., Tranexamic acid, 68-Aminocapronic acid, Alginic acid, Bioflavonoide, Ascorbic acid, Thrombin, oxidized Cellulose, Cetraxate, Epinephrine, Ferric chloride, Fibrinogen, Carbazochrome, Adrenochrome, etc. and salts thereof; vasodilators, e.g., Inositol hexanicotinate, Cyclanderate, Cinnarizine, Tolazoline, Acetylcholine, etc. and salts thereof; agents activaing cellular function, e.g., Solcoseryl, Proglumide, Sucralfate, Gefarnate, Nicametate, Glutamine, Aceglutamide aluminum, Ethylcysteine, Chitin, Tocopherol nicotinate, Ubidecarenone, etc. and salts thereof; antiviral agents, e.g., Aciclovir, Idoxuridine, Betrabin, Amantadine, etc. and salts thereof; agents affecting calcium metabolism, e.g., Vitamin D, Endotoxin, Hydroxyapatite, Collagen, Cataboline, 2-Chloroadenosine, Norcardia, Calcitriol, Prostaglandins for alveolar bone, Osteoclast activating factors for alveolar bone, Parathormone for alveolar bone, Calcitonine for alveolar bone, etc. and salts thereof; astringents, e.g., Tannin, Tanninc acid, Zinc fluoride, Sodium fluoride, Strontium fluoride, Potassium nitate, Stannous fluoide, Aluminum potassium sulfate, Berberine, Bismuth compounds, Strontium chloride, Aluminum lactate, etc. and salts thereof; and the like.

The amount of these topical drugs to be incorporated in the oral preparation varies depending on the kind thereof, but from considerations of pharmacological effects and adhesion to the mucous membrane, it usually ranges from 0.0001 to 35% by weight, and preferably from 0.0002 to 20% by weight, based on the preparation. When positive administration of the drug to the oral mucosa is expected, the drug is preferably present in the adhesive film side. In the treatment of bad breath, and the like, it may be present in the support side.

The composite film composed of the adhesive film and the support has enhanced strength while retaining the excellent adhesion of long duration. As an additional effect, the composite film can prevent adhesion of foreign matters, such as foods, onto the back side of the oral bandage or oral preparations. Further, use of a substantially water-impermeable support effectively prevents permeation of water through the back side to thereby prolong the duration of adhesion.

The adhesive film or support of the oral bandage or oral preparations according to the present invention may further contain other additives, such as coloring matters, flavoring materials, softening agents, and the like, as long as they do not impair adhesiveness or pharmacological effects. For example, when both the adhesive film and the support are colorless, incorporation of a coloring matter in either one of which makes it easy to distinguish the surface or back of the bandage or preparations.

According to the present invention, both of the adhesive film and the composite film composed of the adhesive film and a support are rich in softness and, when applied to the oral mucosa, absorb water in the oral cavity to get further softened. Therefore, they can be easily fitted to any site of the oral cavity to thereby produce strong adhesion for an extended period of time. The adhesive strength of the adhesive film or the composite film of the invention was measured using a cross-linked collagen swollen with water as a substitute for the oral mucosa at a peel angle of 180° and, as a result, was found to be from 25 to 200 g/2.5 cm-width. Adhesive strength smaller than 25 g/2.5 cm-width cannot ensure adhesion to the oral mucosa for a long period of time, and that greater than 200 g/2.5 cm-width is liable to injure the mucous membrane upon peeling. Taking these facts into account, the oral bandage or preparations according to the present invention can be reasonably regarded as exhibiting the optimum adhesive strength.

The above-described adhesive strength is naturally subject to variations depending on the kind of adherends. That is, the adhesive film exerts sufficient adhesion to mucous membranes, the teeth, the skin, cross-linked collagen films, and the like, with the adhesive strength being not impaired even when immersed in water. Whereas, the adhesive film scarcely shows adhesion to plastics, cellophane, etc. If any, the adhesive strength obtained is very weak and rapidly disappears in water. This property is entirely favorable for storage of products. Any special moistureproof packaging is unnecessary because the products do not adhere to packaging materials, storage cases, etc. Further, it is not necessary to cut the oral bandage or oral preparations into small lengths for storage, and they can be formed in a tape and wound on a spool without sticking to each other. They may be stored as they are, but if there is a fear of contamination, the surface that is to show adhesion can be protected with paper or a plastic film.

The oral bandage and oral preparations containing a basic substance for neutralization according to the present invention are highly safe from harm on the injured part of the oral cavity due to the irritant polycarboxylic acids which is dissolved out when applied to the injured parts. That is, the adhesive film of the invention containing no basic substance for neutralization may be applied to the skin of shaved guinea pigs, the eye mucous membrane of rabbits, the oral mucosa of healthy persons, etc. without causing any substantial irritation. However, irritation is noted when it is applied to the injured skin of a shaved guinea pig caused by stripping the corneum with an adhesive tape. To the contrary, the products containing a basic substance for neutralization cause substantially no irritation on such an injured skin as well as on the normal mucous membranes.

The oral bandages or preparations according to the present invention possess excellent water resistance attributed to substantial water-insolubilization of the polycarboxylic acids constituting the adhesive film so that they are only swollen but not degraded even when immersed in water. Therefore, they retain adhesiveness for a long period of time, generally 3 to 4 hours or even more, e.g., for one day, onto the oral mucosa.

Further, the oral preparations comprising the oral bandage of the invention having incorporated therein a topical drug are effective in producing pharmacological effects and very easy to handle since they can be adhered to the wet surface of affected parts of the oral cavity simply by pressing thereonto for the prevention or treatment of oral diseases.

This invention will now be illustrated in greater detail with reference to the following examples, but it should be understood that they are not intended to limit the present invention. In these examples, all the parts and percents are given by weight unless otherwise indicated.

EXAMPLE 1

Five parts of a carboxyvinyl polymer as a polycarboxylic acid and 5 parts of polyvinyl acetate (degree of polymerization: ca. 1,500) were poured in 90 parts of methanol as a common solvent, followed by mixing to form a uniform solution. The resulting solution was flow-casted on a release paper, dried, and peeled off to obtain an adhesive film having a thickness of 30 μm. The value A of this film was 31.3. The dissolution ratio of the polycarboxylic acid, that is a criterion of the compatible state, was 9%, indicating that the film had a compatible state.

The adhesive film thus prepared was laminated on 15 μm thick aluminum foil by hot pressing to obtain an oral bandage.

COMPARATIVE EXAMPLE 1

Five parts of polyvinyl acetate (degree of polymerization: ca. 1,500) were dissolved in 20 parts of toluene, and to the solution was added 5 parts of a toluene-insoluble carboxyvinyl polymer, followed by thoroughly stirring to prepare a uniform suspension. The suspension was then flow-casted on a release paper, dried, hot pressed and peeled off to obtain an adhesive film having a thickness of 30 μm. The resulting film had the same value A as in Example 1 but a ratio of dissolution of the polycarboxylic acid of 67%, which indicated that the carboxylvinyl polymer and the polyvinyl acetate were in a phase-separated state.

The adhesive film thus prepared was laminated on 15 μm thick aluminum foil by hot pressing to obtain an oral bandage.

COMPARATIVE EXAMPLE 2

Five parts of a carboxyvinyl polymer were dissolved in 45 parts of pure water. Separately, 5 parts of polyvinyl acetate (degree of polymerization: ca. 1,500) was dissolved in 20 parts of toluene. The both solutions were mixed and then stirred in a small-sized stirrer at 5,000 rpm for 3 minutes to obtain a suspension. The resulting suspension was flow-casted on a release paper, dried and peeled off to obtain an adhesive film having a thickness of 30 μm. The value A of this film was the same as in Example 1, but the dissolution ratio of the polycarboxylic acid was 79%, indicating that the carboxyvinyl polymer and polyvinyl acetate were in a phase-separated state.

The resulting film was laminated on 15 μm thick aluminum foil by hot pressing to obtain an oral bandage.

The compatible state of each of the samples obtained in the foregoing examples was evaluated by macroscopic observation to see the appearance of the film and also under an optical microscope to observe whether small independent regions of the polycarboxylic acid or polyvinyl acetate were formed or not. Formation of such small regions indicates phase separation.

Further, each of the samples was cut in a size of 5×5 cm, immersed in water at 37° C. for 10 minutes, dreid and weighed to determine weight reduction. The weight reduction (%) as an average of 10 runs was taken as a parameter of solubility of the film.

Furthermore, the dissolution ratio of the polycarboxylic acid after 2 hour- and 4-hour immersion in the same manner as described above for the dissolution ratio after 1 hr-immersion.

The results obtained are shown in Table 1 below. In Table 1, the solubility (weight reduction) is an average of 10 sample pieces. The dissolution ratio after 1 hr-immersion as measured in the foregoing examples is also shown in Table 1.

TABLE 1

|  | Example 1 | Comparative Example 1 | Comparative Example 2 |
|---|---|---|---|
| Compatible State: |  |  |  |
| Appearance | transparent | turbid | turbid |
| Formation of Small Regions | no small regions observed | small regions observed | small regions observed |
| Solubility (%) | 0.1 | 6.9 | 7.7 |
| Dissolution Ratio (%): |  |  |  |
| 1 Hr-Immersion | 9 | 67 | 79 |
| 2 Hr-Immersion | 10 | — | — |
| 4 Hr-Immersion | 12 | — | — |

As is apparent from Table 1 above, in the adhesive film of Example 1, the polycarboxylic acid and polyvinyl acetate are in a good compatible state, making a contrast to those of Comparative Examples 1 and 2. In particular, the results of polycarboxylic acid dissolution ratios reveal that the most of the polycarboxylic acid, an adhesive component, in the films of Comparative Examples 1 and 2 is dissolved out into water through immersion for one hour, whereas the dissolution ratio of the film of Example 1 after 1 hour-immersion is as low as 9%, which increases only to 12% even by immersion for 4 hours, said ratio showing no further increase through additional immersion, though not shown in Table 1. It can be seen from these results that a major porportion of the total amount of the dissolved polycarboxylic acid is dissolved out during the first one hour-immersion. The change in the proportion of the dissolved amount to the total dissolved amount with time is shown in FIG. 1.

Then, the oral bandages obtained in the foregoing examples were subjected to adhesion test and peel test at a peel angle of 180° C. in accordance with the following test methods.

ADHESION TEST

A sample was cut out round to a diameter of 10 mm. The cut piece was attached to a crosslinked collagen film swollen with water which was fixed on a phenolic resin plate and immersed in water at 37° C. to observe the state of the film.

PEEL TEST

A sample was cut into a strip of 2.5 cm in width and 15 cm in length. The strip was attached to a collagen film and immersed in water in the same manner as in the adhesion test, and a peel strength at a peel angle of 180° C. was measured by means of a Schopper type tensile strength tester.

The results obtained are shown in Table 2 below.

TABLE 2

|  | Example 1 | Comparative Example 1 | Comparative Example 2 |
| --- | --- | --- | --- |
| State of Film And Adhesion in Water | No change observed except a swelling of the periphery. Firmly adhered for 5 hrs. | Remarkable swelling from the periphery. Spontaneously separated from the adherend in 0.5 to 1.5 hrs. | Gradual swelling all over the film. Still adhered for 30 mins but with little adhesion. Spontaneously separated from the adherend in 1.5 to 2.0 hrs. |
| Peel Strength (g/2.5 cm-width): Immersion Time: |  |  |  |
| 10 mins | 110 | 12 | 20 |
| 30 mins. | 105 | unmeasurable | unmeasurable |
| 60 mins. | 95 | " | " |
| 120 mins. | 85 | " | " |
| 240 mins. | 90 | " | " |

As can be seen from Table 2, the samples of Comparative Examples 1 and 2 peel apart from the adherend in the early stage of immersion in water, becoming unmeasurable for peel strength when immersed for 30 minutes. To the contrary, the sample according to the present invention exhibits excellent adhesion in water, with its peel strength after 4 hour-immersion showing about 80% of the initial value. These results prove that the oral bandage of the present invention exerts strong adhesion of extremely long duration.

EXAMPLE 2

A 10% methanolic solution of a carboxyvinyl polymer (CVP) and a 10% methanolic solution of polyvinyl acetate (PVAc) (degree of polymerization: ca. 2,500) were mixed at a CVP to PVAc ratio as shown in Table 3. The mixed solution was flow-casted on a release paper and dried to obtain an adhesive film having a thickness of 20 μm. The value A of each sample thus prepared is shown in Table 3.

The resulting film was laminated on a 50 μm thick film of polyvinyl acetate (degree of polymerization: ca. 2,500) by hot pressing to obtain an oral bandage.

Each of the samples thus obtained was determined for the dissolution ratio of the polycarboxylic acid (immersion time: 1 hour), adhesiveness in water and peel strength at a peel angle of 180° C. after 10 minutes-immersion in accordance with the methods as described in Example 1. The adhesiveness in water was expressed in terms of the time until the sample was spontaneously separated from the adherend. These test results are shown in Table 3.

TABLE 3

| Mixing Ratio (CVP:PVAc) | 2:8 | 3:7 | 5:5 | 7:3 | 8:2 |
| --- | --- | --- | --- | --- | --- |
| Value A | 12.5 | 18.8 | 31.3 | 43.8 | 50.0 |
| Dissolution Ratio (%) | 2 | 5 | 8 | 22 | 35 |
| Adhesion Time (hr) | >8 | >8 | >8 | 3.2 | 1.5 |
| Peel Strength (g/2.5 cm-width) | 20 | 60 | 110 | 160 | 200 |

It can be seen from Table 3 above that when the value A falls within the range of from 15 to 45 with the CVP:PVAc ratio being from 3:7 to 7:3, the films are excellent in both adhesion time and peel strength as well as in dissolution ratio of the polycarboxylic acid, indicating usefulness as an oral bandage. However, the film having a CVP:PVAc ratio of 2:8 has the value A smaller than 15 and shows poor adhesion. On the other hand, the film having a CVP:PVAc ratio of 8:2 has a short adhesion time and a high poplycarboxylic acid dissolution ratio due to the value A exceeding 45. Accordingly, these films out of the scope of the present invention are regarded hard to use with exceptions for special purposes of use.

EXAMPLE 3

Four parts of an alternating copolymer of methyl vinyl ether and maleic anhydride and 6 parts of polyvinyl acetate (degree of polymerization: ca. 1,000) were dissolved in 90 parts of methanol. The resulting solution was flow-casted on a release paper, dried at 80° C. and peeled to obtain an adhesive film having a thickness of 60 μm. The value A of this film was 23.0, and the dissolution ratio (immersion time: 1 hour) was 12%.

The oral bandage thus obtained are cut in a circle having a diameter of 10 mm. The cut piece was adhered to the palatine mucosa of 10 panel members, and the time until the sample was separated apart (peeling time) was determined. As a result, an average peeling time was 4.0 hours.

EXAMPLE 4

Six parts of polyacrylic acid (degree of polymerization: ca. 5000) and 14 parts of partially saponified polyvinyl acetate (degree of saponification: 20 mol%; degree of polymerization: ca. 1,500) were dissolved in 80 parts of methanol, and the resulting solution was flow-casted on a release paper, dried at 80° C. and peeled off to obtain an adhesive film having a thickness of 70 μm. The value A of this film was 37.5, and the dissolution ratio of the polycarboxylic acid (immersion time: 1 hour) was 37%.

Separately, an ethylene-vinyl acetate copolymer (vinyl acetate content: 30 mol%) was hot-pressed to form a film support having a thickness of 80 μm. The above obtained adhesive film and the film support were laminated by the use of a hot laminator to produce an oral bandage.

The resulting oral bandage was cut in a strip of 7 mm in width and 20 mm in length. The cut piece was adhered to the gingival mucosa of 10 panel members, and the time until the strip was separated therefrom (peeling time) was measured. As a result, an average peeling time was 7.6 hours.

EXAMPLE 5

Four parts of a carboxyvinyl polymer and 6 parts of polyvinyl acetate (degree of polymerization: ca. 2,000) were dissolved in 92 parts of isopropanol, and 2 parts of titanium dioxide was added thereto as a coloring matter was added thereto, followed by thoroughly mixing with stirring. The mixture was flow-casted on a release paper, dried at 90° C. and peeled off to obtain an adhesive film having a thickness of 15 μm. The value A of this film was 25, and the dissolution ratio of the polycarboxylic acid (immersion time: 1 hour) was 6%. Separately, 0.1 part of Food Red 3 aluminum lake was added to 100 parts of a 20% ethyl acetate solution of polyvinyl acetate (degree of polymerization: ca. 2,000), followed by thoroughly mixing while stirring. The mixture was flow-casted on a release paper, dried at 180° C. and peeled off to prepare a film support having a thickness of 30 μm. The above prepared adhesive film and the film support were laminated by hot pressing to obtain an oral bandage.

The thus obtained oral bandage was cut in a circle having a diameter of 20 mm. The cut piece was adhered to the buccal mucosa of 10 panel members, and the time until the bandage was separated therefrom (peeling time) was determined. As a result, an average peeling time was 5.6 hours.

The performance of the oral bandage to prevent running-off of a drug administered was evaluated using a food dye as a model of a drug and a crosslinked collagen film swollen with water as an adherend as follows. That is, 9.5 parts of lactose and 5 parts of Food Red 102 were ground in a mortar, and the mixture was pounched out into tablets of 5.0 mm in diameter and 0.5 mm in thickness. One of the tablets was placed on a water-swollen crosslinked collagen film that was fixed on a phenolic resin plate, and the oral bandage cut round to a diameter of 15 mm was adhered thereonto so as to cover the tablet. The sample was then immersed in water at 37° C. As a result, the time required for the dye in the tablet to be dissolved out into water was 4.1 hours as an average of 10 runs, indicating a sufficient performance property to prevent runningoff of a drug administered.

Thereafter, the storage stability of the oral bandage was evaluated as follows. The oral bandage was cut in a tape of 18 mm in width and 3 m in length. The tape was rolled up, wrapped with a cellophane film, packed in a paper box of 6 cm×6 cm×2 cm and preserved under ambient conditions for 3 months. A a result, no change in shape or adhesion properties was noted to confirm excellent storage stability of the oral bandage.

EXAMPLE 6

Three parts of a carboxyvinyl polymer, 2 parts of a methyl vinyl ether-maleic anhydride copolymer and 5 parts of polyvinyl acetate (degree of polymerization: ca. 2,000) were dissolved in 90 parts of methanol. The resulting mixed solution was flow-casted on a release paper, dried at 60° C. and peeled off to obtain an adhesive film having a thickness of 15 μm. The value A of this film was 30.3, and the dissolution ratio of the polycarboxylic acid (immersion time: 1 hour) was 10%.

The thus obtained film was laminated on a 30 μm thick film support of polyvinyl acetate (degree of polymerization: ca. 1,500) by hot pressing to obtain an oral bandage.

The resulting oral bandage was cut round to a diameter of 10 mm, adhered to the gingival mucosa of 10 panel members, and the time until the bandage was separated therefrom (peeling time) was measured. As a result, the peeling time was 5.4 hours in average.

EXAMPLE 7

Into 90 parts of methanol were poured 4.7 parts of a carboxyvinyl polymer and 4.7 parts of polyvinyl acetate (degree of polymerization: ca. 1,500), and 0.6 part of diisopropanolamine was further added thereto, followed by mixing to form a uniform solution. The resulting solution was flow-casted on polyethylene-laminated paper dried in a drier at 80° C. for 8 minutes and peeled off to prepare an adhesive film having a thickness of 40 μm. The value A of this film was 31, and the dissolution ratio of the polycarboxylic acid was 12%, which value indicated the compatible state of the film.

The thus obtained adhesive film was laminated on a 40 μm polyvinyl acetate film (degree of polymerization: ca. 2,000) by hot pressing at 100° C. to obtain an oral bandage.

COMPARATIVE EXAMPLE 3

In 30 parts of toluene were dissolved 4.7 parts of polyvinyl acetate (degree of polymerization: ca. 1,500) and 0.6 parts of diisopropanolamine, and 5 parts of a toluene-insoluble carboxyvinyl polymer powder was added to the solution, followed by sufficiently mixing while stirring to prepare a uniformly dispersed suspension. The resulting suspension was flow-casted on polyethylene-laminated paper dried in a drier at 100° C. for 10 minutes and peeled off to obtain an adhesive film having a thickness of 40 μm. The value A of this film was equal to that of the adhesive film of Example 7, but the dissolution ratio of the polycarboxylic acid, that was a creterion of a compatible state, was 72%, indicating that the carboxyvinyl polymer and the polyvinyl acetate were in a phase-separated state.

The adhesive film thus obtained was laminated on a 40 μm thick polyvinyl acetate film by hot pressing at 100° C. in the same manner as in Example 7 to obtain an oral bandage.

COMPARATIVE EXAMPLE 4

In 45 parts of pure water were dissolved 4.7 parts of a carboxyvinyl polymer and 0.6 part of diisopropanolamine. Separately, 4.7 parts of polyvinyl acetate (degree of polymerization: ca. 1,500) was dissolved in 30 parts of toluene. The two solutions were mixed and stirred in a small-sized stirrer at 5,000 rpm for 5 minutes to prepare a suspension. The resulting suspension was flow-casted on polyethylene-laminated paper, dried in a drier at 100° C. and peeled off to obtain an adhesive film having a thickness of 40 μm. The value A of this film was equal to that of the film of Example 7, but the dissolution ratio of the polycarboxylic acid was 77%, indicating that the carboxyvinyl polymer and the polyvinyl acetate were in a phase-separated state.

The film thus obtained was laminated on a 40 μm thick polyvinyl acetate film by hot pressing at 100° C. in the same manner as in Example 7 to obtain an oral bandage.

Each of the samples obtained in Example 7 and Comparative Examples 3 and 4 was evaluated for the compatible state, the adhesiveness (adhesion time) and the peel strength. The compatible state was observed in the same manner as in Example 1, and the adhesiveness and peel strength were determined in the same manner as in Example 2. Further, each sample cut round to a diameter of 10 mm was adhered to the palatine mucosa of 5 healthy male panel members, and the time until the sample was separated therefrom was measured. The adhesion was effected after lunch, and the panel members were allowed to drink and talk, ad lib. The results obtained are shown in Table 4 below.

TABLE 4

|  | Example 7 | Comparative Example 3 | Comparative Example 4 |
| --- | --- | --- | --- |
| Compatible State: |  |  |  |
| Appearance | transparent | turbid | turbid |
| Formation of Small Regions | no small regions observed | small regions observed | small regions observed |
| Adhesiveness (Adhesion Time) (min) | 185(1) | 70(2) | 55(2) |
| Peel Strength (g/2.5 cm-width) | 35 | 10 | 12 |
| Peeling Time (min) | 210 | 25 | 40 |

Note
(1)Strong adhesion was retained for 60 minutes.
(2)Only slight adhesion was noted with insubstantial adhesive strength after 60 minutes.

As is apparent from the results of Table 4, the polycarboxylic acid and the polyvinyl acetate in the film of Example 7 are in a good compatible state, making a contrast to the films of Comparative Examples 3 and 4. More specifically, the films of Comparative Examples 3 and 4 are separated from the adherend in the early stage of the adhesion test and undergo great reduction in adhesion through immersion in water for 10 minutes in the peel test. Further, these comparative samples are separated from the adherend in the test using a panel. To the contrary, the oral bandage according to the present invention exhibits excellent results in the adhesion test, peel test and panel test, demonstrating strong adhesion of long duration.

COMPARATIVE EXAMPLE 5

In order to ascertain high safety of the oral bandage of the present invention, a comparative adhesive film containing no diisopropanolamine was prepared as follows.

| Carboxyvinyl polymer | 5.0 parts |
| --- | --- |
| Polyvinyl acetate (degree of polymerization: ca. 2,000) | 5.0 parts |
| Methanol | 90.0 parts |

The above components were mixed while stirring to prepare a uniform solution. The solution was flow-casted on polyethylene-laminated paper, dried in a drier at 80° C. for 8 minutes and peeled off to obtain an adhesive film having a thickness of 40 μm. The resulting film was laminated on a 40 μm thick polyvinyl acetate film (degree of polymerization: ca. 2,000) by hot pressing at 100° C. to obtain a comparative oral bandage.

Irritation of the oral bandage as obtained in Example 7 on the normal skin and injured skin of a guinea pig was determined as compared with the above obtained comparative sample in accordance with the following test method.

The back of female Hartley guinea pigs (body weight: 300 to 400 g) was shaved with an electric clipper and an electric shaver to expose the normal skin. An adhesive tape was attached to the normal skin followed by peeling 7 times, whereby the stratum corneum was removed therefrom to form injured skin.

The sample was cut round to a diameter of 10 mm, dipped in water and adhered to each of the normal skin and the injured skin. The adhered sample was covered with absorbent cotton and further closely covered thereon with an adhesive tape for tight covering. Six hours later, the sample was removed, and irritation score was judged after 1 hour and 24 hours from the removal according to the following four grades:
0: No change
0.5: Slight Erythema
1: Moderate Erythema
2: Severe erythema with edema The results obtained are shown in Table 5 below. Each score shown in Table 5 is an average of 6 runs.

TABLE 5

|  | Normal Skin | | Injured Skin | |
| --- | --- | --- | --- | --- |
|  | 1 Hr | 24 Hrs | 1 Hr | 24 Hrs |
| Example 7 | 0.3 | 0.3 | 0.5 | 0.5 |
| Comparative Example 5 | 0.3 | 0.4 | 0.4 | 2.0 |
| Non-Treated Group | 0.1 | 0.2 | 0.2 | 0.3 |

The results of Table 5 above demonstrate that the sample according to the present invention causes no irritation on not only the normal skin but the injured skin as compared with the comparative sample, although there is no difference in irritation on the normal skin between the sample of the invention and the comparative sample.

EXAMPLE 8

| Carboxyvinyl polymer | 8.0 parts |
| --- | --- |
| Polyvinyl acetate (degree of polymerization: ca. 1,500) | 2.0 parts |
| ZnO | 3.6 parts |
| Methanol | 26.4 parts |

The above components were kneaded to obtain a uniform mixture. The mixture was flow-casted on polyethylene-laminated paper having been subjected to releasability-imparting treatment, dried in a drier at 100° C. for 3 minutes and peeled off to obtain an adhesive film having a thickness of 10 μm. The value A of this film was 50. The resulting film was then laminated on a 40 μm thick film of a mixture of polyvinyl acetate (degree of polymerization: ca. 800) and polybutene (95:5) by hot pressing at 100° C. to obtain an oral bandage.

The sample was evaluated for peel strength, peeling time (panel test) and irritation on the injured skin in the same manner as for the sample of Example 7. The results obtained are as follows:
Peel Strength: 60 g/2.5 cm-width
Peeling Time: 186 minutes
Irritation Score: 0.6

EXAMPLE 9

| Carboxyvinyl polymer | 3.4 parts |
| --- | --- |
| Polyvinyl Acetate (Degree of polymerization: ca. 1,000) | 8.4 parts |
| Sodium citrate (Na$_3$C$_6$H$_5$O$_7$) | 0.2 part |
| Methanol | 71.0 parts |
| Pure water | 17.0 parts |

The above components were mixed to obtain a uniform solution, and the solution was flow-casted on a polyethylene terephthalate film, dried in a drier at 80° C. for 15 minutes and peeled off to obtain an adhesive film having a thickness of 80 μm. The value A of this film was 18. The resulting film was then laminated on 15 μm thick aluminum foil by hot pressing at 100° C. to obtain an oral bandage.

The sample was evaluated for peel strength, peel time (panel test) and irritation on the injured skin in the same manner as for the sample of Example 7. The results obtained are as follows:
Peel Strength: 25 g/2.5 cm-width
Peeling Time: 258 minutes
Irritation Score: 0.3

EXAMPLE 10

| Methyl vinyl ether/maleic anhydride alternating copolymer | 4.0 parts |
| --- | --- |
| Polyvinyl acetate (degree of polymerization: ca. 1,500) | 6.0 parts |
| Sodium hydroxide | 0.5 part |
| Methanol | 67.5 parts |
| Eethyl acetate | 22.0 parts |

The above components were mixed to prepare a uniform solution, and the solution was flow-casted on 15 μm thick aluminum foil and dried in a drier at 60° C. for 15 minutes to obtain a composite oral bandage having a total thickness of 35 μm. The value A of the adhesive film constituting the composite oral bandage was 23.

The sample was evaluated for peel strength, peeling time (panel test) and irritation on the injured skin in the same manner as for the sample of Example 7. The results obtained are as follows:
Peel Strength: 54 g/2.5 cm-width
Peeling Time: 222 minutes
Irritation Score: 0.5

EXAMPLE 11

| Polyacrylic acid | 7.0 part |
| --- | --- |
| Saponified polyvinyl acetate (saponification degree: 20 mol %) | 3.0 parts |
| ZnO | 0.8 part |
| Methanol | 89.2 parts |

The above components were mixed to prepare a uniform solution. The solution was flow-casted on polyethylene-laminated paper, and dried in a drier at 80° C. for 10 minutes to obtain a composite oral bandage having a thickness of 50 μm. The value A of the adhesive film constituting the composite was 44.

The sample was evaluated for peel strength, peeling time (panel test) and irritation on the injured skin in the same manner as for the sample of Example 7. The results obtained are as follows:
Peel Strength: 70 g/2.5 cm-width
Peeling Time: 166 minutes
Irritation Score: 1.0

EXAMPLE 12

| Carboxyvinyl polymer | 4.0 parts |
| --- | --- |
| Polyvinyl acetate (degree of polymerization: ca. 2,000) | 6.0 parts |
| Diisopropanolamine | 0.7 part |
| ZnO | 1.4 parts |
| Methanol | 87.9 parts |

The above components were mixed to prepare a uniform solution. The solution was flow-casted on a polyethylene terephthalate film, dried in a drier at 80° C. for 15 minutes and peeled off to obtain an adhesive film having a thickness of 30 μm. The value A of this film was 25.

| Polyvinyl acetate (degree of polymerization: ca. 2,000) | 80.0 parts |
| --- | --- |
| Titanium white | 19.5 parts |
| Food Red 3 aluminum lake | 0.5 part |

The above components were mixed and formed into a film of 30 μm in thickness, and the above prepared adhesive film was laminated thereon by hot pressing at 100° C. to obtain an oral bandage.

The resulting sample was evaluated for peel strength, peeling time (panel test) and irritation on the injured skin in the same manner as for the sample of Example 7. The results obtained are as follows:
Peel Strength: 35 g/2.5 cm-width
Peeling Time: above 300 minutes
Irritation Score: 0.4

EXAMPLE 13

| Carboxyvinyl polymer | 3.0 parts |
| --- | --- |
| Methyl vinyl ether/maleic anhydride alternating copolymer | 2.0 parts |
| Polyvinyl acetate (degree of polymerization: ca. 1,500) | 4.3 parts |
| Triethanolamine | 0.7 part |
| Methanol | 80.0 parts |
| Pure water | 10.0 parts |

The above components were mixed to prepare a uniform solution. The solution was flow-casted on polyethylene-laminated paper, dried in a drier at 80° C. for 10 minutes and peeled off to obtain an adhesive film having a thickness of 25 μm. The value A of this film was 33.

The resulting film was laminated on a 30 μm thick polyvinyl acetate film (degree of polymerization: ca. 1,500) by hot pressing at 100° C. to obtain an oral bandage.

The resulting sample was evaluated for peel strength, peeling time (panel test) and irritation on the injured skin in the same manner as for the sample of Example 7. The results are as follows:

Peel Strength: 42 g/2.5 cm-width
Peeling Time: 190 minutes
Irritation Score: 0.4

EXAMPLES 14 to 19

Oral preparations comprising an adhesive film or a composite of an adhesive film and a support, in which the adhesive film and/or the support contained a topical drug as shown in Table 6 below, were prepared using the materials shown in Table 6. In each example, the adhesive film and the support were prepared in the same manner as described in the corresponding example shown in the column of "material" in Table 6 except for film thickness.

TABLE 6

| Example No. | Adhesive Film | | | Support | | |
|---|---|---|---|---|---|---|
| | Material | Drug and Its Content (wt %) | Thickness (μm) | Material | Drug and Its Content (wt %) | Thickness (μm) |
| 14 | Example 1 | Mepivacaine 5 | 30 | Example 1 | — | 15 |
| 15 | Example 2 (CVP/PVAc = 5/5) | — | 20 | Example 2 | Cetylpyridinium chloride 2 l-Menthol 3 | 50 |
| 16 | Example 3 | Lithospermi Radix extract | 60 | PVAc* | — | 30 |
| 17 | Example 4 | Chlorhexidine-hydrochloride 2 | 100 | — | — | — |
| 18 | Example 5 | Predonisolone 0.2 | 40 | Example 5 | — | 30 |
| 19 | Example 6 | Sodium azulene-sulfonate 0.5 | 20 | Example 6 | — | 30 |

Note: *Polyvinyl acetate having a degree of polymerization of about 2,000.

EXAMPLES 20 to 37

Oral preparations comprising an adhesive film and a support, in which the adhesive film or both the adhesive film and the support contained a topical drug as shown in Table 7 below, were prepared using the film materials shown in Table 7. In each example, the adhesive film and the support were prepared in the same manner as described in the corresponding example shown in the column of "material" in Table 7 except for film thickness.

TABLE 7

| Example No. | Adhesive Film | | | Support | | |
|---|---|---|---|---|---|---|
| | Material | Drug and Its Content (wt %) | Thickness (μm) | Material | Drug and Its Content (wt %) | Thickness (μm) |
| 20 | Example 7 | Triamcinolone acetonide 0.05 | 30 | Example 7 | — | 40 |
| 21 | Example 7 | Dipotassium glycyrrhetinate 1.0 | 30 | Example 7 | — | 40 |
| 22 | Example 7 | Fradiomycin sulfate 1.0 Hydrocortisone acetate 0.5 | 30 | Example 7 | — | 40 |
| 23 | Example 7 | Ethyl aminobenzoate 10.0 | 30 | Example 7 | — | 40 |
| 24 | Example 7 | Tocopherol nicotinate 2.0 Cetylpyridinium chloride 0.2 | 30 | Example 7 | — | 40 |
| 25* | Example 8 | Tetracycline hydrochloride 3 | 20 | Example 8 | — | 30 |
| 26* | Example 8 | Strontium chloride 5 | 20 | Example 8 | — | 30 |
| 27* | Example 8 | Tranexamic acid 0.1 | 20 | Example 8 | — | 30 |
| 28 | Example 9 | Dexamethasone 0.1 | 60 | Example 9 | — | 9 |
| 29 | Example 9 | Sodium fluoride 5 | 60 | Example 9 | — | 9 |
| 30 | Example 9 | Lysozyme chloride 0.5 | 60 | Example 9 | — | 9 |
| 31 | Example 11 | Lidocaine 5 | 50 | Ethylene-vinyl acetate copolymer (vinyl acetate content: 28 wt %) | — | 60 |
| 32 | Example 12 | Aluminum lactate 5 | 60 | Example 12 | — | 30 |

TABLE 7-continued

| Example No. | Adhesive Film | | | Support | | |
|---|---|---|---|---|---|---|
| | Material | Drug and Its Content (wt %) | Thickness (μm) | Material | Drug and Its Content (wt %) | Thickness (μm) |
| 33 | Example 13 | Dibucaine hydrochloride 0.5 | 30 | Example 13 | Dibucaine hydrochloride 0.5 | 30 |
| 34 | Example 13 | Dequalinium hydrochloride 2 | 30 | Example 13 | Dequalinium hydrochloride 2 | 30 |
| 35 | Example 13 | Calcitriol 0.001 | 40 | Example 13 | — | 30 |
| 36 | Example 13 | 1α,(OH)—vitamin D₃ 0.005 | 40 | Example 13 | — | 30 |
| 37 | Example 13 | 1α,24(R)—(OH)₂—vitamin D₃ 0.005 | 40 | Example 13 | — | 30 |

*Dried at 70° C. for 15 minutes

The effects of the oral preparations obtained in Example 14 to 37 were evaluated by the following clinical examples.

CLINICAL EXAMPLE 1

Effect on Stomatitis

A patient (50-year-old, female) suffered from stomatitis of 5 mm in diameter on her buccal mucosa. The oral preparation of Example 20 was applied on the affected part three times a day. The inflammation subsided on the third day.

CLINICAL EXAMPLE 2

Effect on Stomatitis

A patient (27-year-old, male) with stomatitis of 6 mm in diameter on his gingival mucosa, who had much pain at meals. The oral preparation of Example 3 was prescribed to him with a direction to apply to the affected part at meals. He had no pain on the injured site during a meal.

CLINICAL EXAMPLE 3

Effect on the injured site by toothbrushing

A patient (8-year-old, female) had a injured site on her gingival mucosa due to brushing with a tooth-brush. The oral preparation of Example 21 was applied to the injured part three times a day, while toothbrushing instructions were given to the patient. The wound healed on the 2nd day.

CLINICAL EXAMPLE 4

Effect on Halitosis

A patient (21-year-old, female) complained of bad breath. Ten oral bandages of Example 15 were prescribed to her with directions to apply to the cervix dentis of the jaw twice a day. On re-examination after 1 week, subjective symptoms disappeared.

CLINICAL EXAMPLE 5

Prophylactic Effect on Infection

456 Flap operation was performed on a patient (39-year-old, male) with adult periodontitis having deep pockets.

The oral preparation of Example 22 was applied on the operated part, and a pack was further applied thereon. When the pack was removed on the third day, granulation was found to be normal. The patient further received only the oral preparation twice a day for 4 days, and the postoperative course was uneventful.

CLINICAL EXAMPLE 6

Effect on Periodontal Disease

The oral preparation of Example 24 was applied to 345 of a patient (45-year-old, male) with adult periodontitis having deep pockets once a day for 4 weeks. As a control, 345 were not treated with the oral preparation.

As a result, in the treated part, the gingival index decreased from 2 to 1 and the pocket depth decreased from 5.5 mm to 4.0 mm. On the other hand, almost no improvement of symptoms was noted in the control part.

CLINICAL EXAMPLE 7

Effect on Dentin Hyperesthesia

A patient (36-year-old, female) complained of dentin hyperesthesia accompanied by sharp pain in 4. Thirty units of the oral preparation of Example 26 were prescribed to her with a direction to apply to the affected part twice a day.

On re-examination after 3 weeks, the symptoms completely disappeared.

CLINICAL EXAMPLE 8

Effect on dentin hyperesthesia

A patient (56-year-old, female) complained of dentin hyperesthesia accompanied by sharp pain in 2. The oral preparation of Example 9 were applied to the affected part twice a day.

On re-examination after four weeks, the symptoms completely disapperred.

CLINICAL EXAMPLE 9

Local Anesthetic Effect

The oral preparation of Example 31 was preoperatively applied to the gingiva of a patient (41-year-old, female) with proliferative gingivitis. Thereafter, gingivectomy was performed on the patient, but the patient experienced neither pain during the operation nor paresthesia in the part where the oral preparation was not administered. Further, the postoperative course was uneventful.

While the invention has been described in detail and with reference to specific embodiments thereof, it will be apparent to one skilled in the art that various changes and modifications can be made therein without departing from the spirit and scope thereof.

What is claimed is:

1. An oral bandage comprising a soft adhesive film having a thickness of at least 5 μm consisting essentially of a polycarboxylic acid and/or a polycarboxylic acid anhydride and a vinyl acetate polymer in a compatible state, wherein the polycarboxylic acid and/or the polycarboxylic acid anhydride and the vinyl acetate polymer are uniformly dissolved in each other without forming individual regions due to phase separation.

2. An oral bandage as in claim 1, wherein a mixing ratio of the polycarboxylic acid and/or polycarboxylic acid anhydride to vinyl acetate polymer is such that the value as obtained from the following formula ranges from 15 to 45:

$$\frac{\left(\begin{array}{c}\text{Weight of —COOH}\\\text{in Adhesive Film}\end{array}\right)+\frac{5}{4}\left(\begin{array}{c}\text{Weight of —CO—O—CO—}\\\text{in Adhesive Film}\end{array}\right)}{\text{Weight of Polycarboxylic Acid and/or Polycarboxylic Acid Anhydride in Adhesive Film + Weight of Vinyl Acetate Polymer in Adhesive Film}} \times 100$$

3. An oral bandage as in claim 1, wherein said mixture in a compatible state is obtained by dissolving the polycarboxlyic acid and/or polycarboxylic acid anhydride and the vinyl acetate polymer in a solvent common to both.

4. An oral bandage as in claim 1, wherein said oral bandage further comprises a soft film support.

5. An oral bandage as in claim 1, wherein said adhesive film further comprises a basic substance capable of neutralizing the polycarboxylic acid and/or polycarboxylic acid anhydride in an amount which is effective to relieve irritation to an injured part.

6. An oral bandage as in claim 5, wherein said basic substance is at least one of salts and bases.

7. An oral bandage as in claim 5, wherein said oral bandage further comprises a soft film support.

8. An oral bandage as in claim 1, wherein said polycarboxylic acid contains 20% by weight or more of a —COOH group and said polycarboxylic acid anhydride contains 16% by weight or more of a —CO—O—CO— group.

9. An oral bandage as in claim 6, whwerein said basic substance is a monovalent metal salt or monovalent base and is used in an amount of from 0.03 to 0.2 equivalent based on the polycarboxylic acid and/or polycarboxylic acid anhydride.

10. An oral bandage as in claim 3, wherein said solvent is selected from lower alcohols, mixed solvents comprising a lower alcohol in a larger proportion and a compatible organic solvent, mixed solvent of a lower alcohol in a larger proportion and water, and a mixed solvent comprising a lower alcohol in a larger proportion, a compatible organic solvent and water.

11. An oral bandage as in claim 10, wherein said mixed solvent of a lower alcohol and an organic solvent contains not more than 30% by weight of the organic solvent.

12. An oral bandage as in claim 10, wherein said mixed solvent of a lower alcohol and water or mixed solvent of a lower alcohol, an organic solvent and water contains not more than 30% by weight of water.

13. An oral preparation comprising a soft adhesive film having a thickness of at least 5 μm consisting essentially of a mixture of a polycarboxylic acid and/or a polycarboxylic acid anhydride and a vinyl acetate polymer in a compatible state and topical drug incorporated therein, wherein the polycarboxylic acid and/or the polycarboxylic acid anhydride and the vinyl acetate polymer are uniformly dissolved in each other without forming individual regions due to phase separation.

14. An oral preparation as in claim 13, wherein a mixing ratio of the polycarboxylic acid and/or polycarboxylic acid anhydride to vinyl acetate polymer is such that the value as obtained from the following formula ranges from 15 to 45:

$$\frac{\left(\begin{array}{c}\text{Weight of —COOH}\\\text{in Adhesive Film}\end{array}\right)+\frac{5}{4}\left(\begin{array}{c}\text{Weight of —CO—O—CO—}\\\text{in Adhesive Film}\end{array}\right)}{\text{Weight of Polycarboxylic Acid and/or Polycarboxylic Acid Anhydride in Adhesive Film + Weight of Vinyl Acetate Polymer in Adhesive Film}} \times 100$$

15. An oral preparation as in claim 13, wherein said mixture in a compatible state is obtained by dissolving the polycarboxylic acid and/or polycarboxylic acid anhydride and the vinyl acetate polymer in a solvent common to both.

16. An oral preparation as in claim 13, wherein said adhesive film further comprises a basic substance capable of neutralizing the polycarboxylic acid and/or polycarboxylic acid anhydride in an amount which is effective to relieve irritation to an injured part.

17. An oral preparation as in claim 16, wherein said basic substance is at least one of salts and bases.

18. An oral preparation as in claim 13, wherein said oral preparation further comprises a soft film support.

19. An oral preparation as in claim 16, wherein said oral preparation further comprises a soft film support.

20. An oral preparation as in claim 18, wherein the film support contains a topical drug.

21. An oral preparation as in claim 19, wherein the film support contains a topical drug.

22. An oral preparation as in claim 13, wherein said polycarboxylic acid contains 20% by weight or more of a —COOH group and said polycarboxylic acid anhydride contains 16% by weight or more of a —CO—O—CO— group.

23. An oral bandage as in claim 13, wherein said vinyl acetate polymer has a viscosity-average molecular weight of not less than 60,000.

24. An oral bandage as in claim 17, wherein said basic substance is a monovalent metal salt or a monovalent base and is used in an amount of from 0.03 to 0.2 equivalent based on the polycarboxylic acid and/or polycarboxylic acid anhydride.

25. An oral bandage as in claim 15, wherein said sovlent is selected from lower alcohols, mixed solvents comprising a lower alcohol in a larger proportion and a compatible organic solvent, mixed solvent of a lower alcohol in a larger proportion and water, and a mixed solvent comprising a lower alcohol in a larger proportion, a compatible organic solvent and water.

26. An oral bandage as in claim 25, wherein said mixed solvent of a lower alcohol and an organic solvent contains not more than 30% by weight of the organic solvent.

27. An oral bandage as in claim 25, wherein said mixed solvent of a lower alcohol and water or mixed solvent of a lower alcohol, an organic solvent and water contains not more than 30% by weight of water.

* * * * *